United States Patent
Kimura et al.

(10) Patent No.: US 6,383,973 B1
(45) Date of Patent: May 7, 2002

(54) COMPLEX OXIDE CATALYSTS AND PROCESS FOR PRODUCING (METH) ACROLEIN AND (METH) ACRYLIC ACID

(75) Inventors: Naomasa Kimura, Okayama; Michio Tanimoto; Hideo Onodera, both of Himeji, all of (JP)

(73) Assignee: Nippon Shokusai Co. Ltd., Osaka (JP)

( * ) Notice: Subject to any disclaimer, the term of this patent is extended or adjusted under 35 U.S.C. 154(b) by 0 days.

(21) Appl. No.: 09/575,454

(22) Filed: May 22, 2000

(30) Foreign Application Priority Data

May 25, 1999 (JP) .......................... 11-144296

(51) Int. Cl.$^7$ .................. B01J 27/14; B01J 27/198; B01J 23/00; B01J 23/58; B01J 23/02
(52) U.S. Cl. ............... 502/300; 502/302; 502/305; 502/308; 502/311; 502/313; 502/317; 502/321; 502/325; 502/330; 502/341; 502/344; 502/349; 502/353; 502/355; 502/208; 502/209; 502/212; 502/213
(58) Field of Search ................. 502/208–215, 502/300–355

(56) References Cited

U.S. PATENT DOCUMENTS

| | | | | |
|---|---|---|---|---|
| 4,219,484 A | * | 8/1980 | Milberger et al. | 260/346.75 |
| 4,537,874 A | * | 8/1985 | Sato et al. | 502/311 |
| 4,803,190 A | | 2/1989 | Sarumaru et al. | 502/205 |
| 4,804,778 A | | 2/1989 | Oh-Kita et al. | |
| 4,863,891 A | * | 9/1989 | Grasselli et al. | 502/306 |
| 4,925,980 A | | 5/1990 | Matsumoto et al. | |
| 5,093,299 A | * | 3/1992 | Suresh et al. | 502/212 |
| 5,153,162 A | * | 10/1992 | Kurimoto et al. | 502/209 |
| 5,364,825 A | * | 11/1994 | Neumann et al. | 502/311 |
| 5,491,258 A | | 2/1996 | Watanabe et al. | |
| 5,618,974 A | * | 4/1997 | Kurimoto et al. | 562/532 |
| 5,681,790 A | | 10/1997 | Kim et al. | |
| 5,840,648 A | * | 11/1998 | Suresh et al. | 502/306 |

FOREIGN PATENT DOCUMENTS

| | | |
|---|---|---|
| EP | 0304867 | 3/1989 |
| GB | 1330074 | 9/1973 |
| GB | 1390271 | 4/1975 |
| GB | 144659 | 8/1976 |
| JP | 5013308 | 2/1975 |
| JP | 5047915 | 4/1975 |
| JP | 5623696 | 6/1981 |
| JP | 5652013 | 12/1981 |
| JP | 62234548 | 10/1987 |
| JP | 6456634 | 3/1989 |

* cited by examiner

*Primary Examiner*—Mark L. Bell
*Assistant Examiner*—Patricia L. Hailey

(57) ABSTRACT

Complex oxide catalysts represented by the formula, $$Mo_aW_bBi_cFe_dA_eB_fC_gD_hE_iO_x$$

(in which A is Ni or Co; B is Na, K, Rb, Cs or Tl; C is an alkaline earth metal; D is P, Te, Sb, Sn, Ce, Pb, Nb, Mn, As, B or Zn; E is Si, Al, Ti or Zr; and where a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$) are provided. The catalysts are characterized in that the molar ratio of the total nitrate anions to the molybdenum at the time of catalyst preparation is more than 1 but not more than 1.8. When used in the reaction for producing (meth) acrolein and (meth)acrylic acid by vapor-phase oxidation of at least a compound selected from propylene, isobutylene, t-butanol and methyl-t-butyl ether, the catalysts exhibit excellent activity and selectivity and maintain stable performance over prolonged period.

9 Claims, No Drawings

COMPLEX OXIDE CATALYSTS AND PROCESS FOR PRODUCING (METH) ACROLEIN AND (METH) ACRYLIC ACID

TECHNICAL FIELD TO WHICH THE INVENTION BELONGS

This invention relates to complex oxide catalysts and process for producing (meth)acrolein and (meth)acrylic acid. More particularly, the invention relates to Mo-Bi-containing complex oxide catalysts which are suitable for use in production of (meth)acrolein and (meth)acrylic acid, and process for producing (meth)acrolein and (meth)acrylic acid by vapor-phase oxidation of at least one compound selected from propylene, isobutylene, t-butanol and methyl-t-butyl ether, in presence of one of said catalysts.

CONVENTIONAL TECHNOLOGY

Many proposals have been made for improved catalysts for vapor phase catalytic oxidation of propylene, isobutylene and the like to produce (meth)acrylic acid and (meth)acrolein. For example, Official Gazette of Sho 50 (1975)-13308A1-JP and Sho 50-47915A1-JP proposed catalysts containing at least an element selected from K, Rb and Cs as one of the essential components, besides Mo, Bi, Fe, Sb and Ni, and Sho 64 (1989)-56634A1-JP proposed those containing at least an element selected from Ni and Co as the essential component, in addition to Mo, Bi and Fe. Also Sho 56 (1981)-52013B1-JP disclosed catalysts containing at least an element selected from Mg, Ca, Zn, Cd and Ba as the essential component, besides Mo, Bi and Fe; and Sho 56-23969B1-JP, catalysts containing at least an element selected from IIA and IIB Group elements as the essential component, besides Mo, Bi and Fe.

In those prior art catalysts, as Bi-supplying source water-soluble compounds thereof, in particular, nitric acid salts are used. However, use of bismuth nitrate as the Bi-supplying source in production of the catalysts of high Bi content (e.g., those in which the atomic ratio of Mo to Bi is, where Mo is 12, Bi is 3–7) is problematical. With the view to solve that problem, Sho 62 (1987)-234548A1-JP has proposed a production method of complex oxide catalysts for which bismuth oxide or bismuth oxycarbonate are used as the Bi-supplying source.

OBJECTS OF THE INVENTION

While prior art Mo-Bi-containing complex oxide catalysts are considered to have overcome the problem incidental to the use of bismuth nitrate, there still remain shortcomings which must be improved. More specifically, for example, ① in the occasions of producing (meth)acrolein and (meth) acrylic acid by vapor-phase oxidation of propylene, isobutylene and the like using those catalysts, yield of the object products is not necessarily satisfactory, and ② due to sublimation of the molybdenum component in the catalysts during the vapor-phase oxidation reaction of propylene, isobutylene and the like, the catalytic activity decreases and the catalysts are unsatisfactory in respect of their life.

One of the objects of the present invention is, therefore, to provide complex oxide catalysts for production of (meth) acrolein and (meth)acrylic acid, which excel in activity, selectivity and catalyst life and exhibit stable performance over prolonged period.

Another object of the invention is to provide a process for producing (meth)acrolein and (meth)acrylic acid at high yield and with stability, by vapor-phase oxidation of at least one compound selected from propylene, isobutylene, t-butanol and methyl-t-butyl ether with molecular oxygen or a molecular oxygen-containing gas in the presence of the above complex oxide catalyst.

MEANS TO SOLVE THE PROBLEM

We have made concentrative studies on complex oxide catalysts to discover that the amount of molybdenum sublimation during vapor phase oxidation reaction of propylene, isobutylene and the like is inhibited when the amounts of bismuth, iron, cobalt and nickel are relatively large. However, it is also discovered that the relatively large amounts of bismuth, iron, cobalt and nickel increase also the amount of nitrate anions at the time of catalyst preparation, which has such adverse effects as deteriorating moldability of catalyst compositions and impairing their catalytic performance. We continued further investigations with the view to solve this problem, to find that the catalysts excelling in activity, selectivity and life can be produced with good reproducibility by reducing the molar ratio of nitrate anions to molybdenum at the time of the catalyst preparation.

Thus, according to the present invention, complex oxide catalysts are provided, which are represented by general formula (1) below:

$$Mo_aW_bBi_cFe_dA_eB_fC_gD_hE_iO_x \quad (1)$$

(wherein Mo is molybdenum; W is tungsten; Bi is bismuth; Fe is iron; A is at least an element selected from nickel and cobalt; B is at least an element selected from sodium, potassium, rubidium, cesium and thallium; C is at least an element selected from alkaline earth metals; D is at least an element selected from phosphorus, tellurium, antimony, tin, cerium, lead, niobium, manganese, arsenic, boron and zinc; E is at least an element selected from silicon, aluminum, titanium and zirconium; and O is oxygen; a, b, c, d, e, f, g, h, i and x denote the atomic ratios of Mo, W, Bi, Fe, A, B, C, D, E and O, respectively; and where a is 12, $0 \leq b \leq 10$, $0 < c \leq 10$ (preferably $0.1 \leq c \leq 10$), $0 < d \leq 10$ (preferably $0 \leq d \leq 10$, $2 \leq e \leq 15$, $0 < f \leq 10$ (preferably $0.001 \leq f \leq 10$), $0 \leq g \leq 10$, $0 \leq h \leq 4$ and $0 \leq i \leq 30$, and x is determined by degree of oxidation of each of the elements), said catalysts being characterized in that the molar ratio of total nitrate anions to molybdenum at the time of catalyst preparation is adjusted to be more than 1 but not more than 1.8.

According to the invention, furthermore, there is provided a process for producing (meth)acrolein and (meth)acrylic acid through vapor-phase oxidation of at least one compound selected from the group consisting of propylene, isobutylene, t-butanol and methyl-t-butyl ether with molecular oxygen or a molecular oxygen-containing gas, in the presence of an oxidation catalyst, the process being characterized in that it uses an above-defined complex oxide catalyst.

EMBODIMENTS IF THE INVENTION

The catalysts of the present invention are complex oxide catalysts, at the time of whose preparation the ratio of the total molar amount of nitrate anions [NO$_3$] to the molar amount of molybdenum [Mo] is adjusted to be more than 1 but not more than 1.8, i.e., $1 < [NO_3]/[Mo] \leq 1.8$. Preferably the ratio is within the range of $1.1 \leq [NO_3]/[Mo] \leq 1.8$.

"Total molar amount of nitrate anions at the time of the catalyst preparation" signifies the sum of the molar amount of nitrate anions contained in all of the starting materials which are used for preparation of the catalyst plus the molar amount of nitrate anions originating from the nitric acid which is used for the catalyst preparation as necessity arises. For example, referring to the later appearing Example 1, it is the total sum of the molar amount of nitrate anions derived from the cobalt nitrate, nickel nitrate, etc., which were used as the starting materials, plus the molar amount of the nitrate anions derived from the nitric acid which was used for dissolving bismuth nitrate.

When the ratio of [$NO_3$] to [Mo] exceeds 1.8, deterioration in moldability and degradation in the catalytic performance result, and the objects of the present invention cannot be accomplished. That is, when such a large amount of nitrate anions is present at the time of the catalyst preparation, pH becomes very low and under the strongly acidic condition, stability and reactivity of molybdenum, tungsten and the like are adversely affected. Furthermore, because the powder obtained through such steps as evaporation to dry solid, drying and grinding contains the large amount of nitrate anions, it absorbs moisture during molding and is apt to invite deterioration in moldability. Whereas, when the ratio of [$NO_3$] to [Mo] is 1 or less, reactivity among the used elements drops, which results in reduction in catalytic activity.

For controlling the ratio of the total molar amount of nitrate anions to that of molybdenum to be more than 1 but not more than 1.8 at the time of catalyst preparation, for example, basic bismuth nitrate is used as at least a part of the bismuth source. "Basic bismuth nitrate" is, while its chemical formula is not necessarily established, also called, for example, bismuth oxynitrate or bismuth oxyhydroxide and has a lower nitrate anions content than that of bismuth nitrate ($Bi(NO_3)_3 \cdot 5H_2O$). For keeping the ratio within the specified range, furthermore, as the sources of other elements, compounds other than nitrates (e.g., compounds containing no or less nitric acid, such as hydroxides, carbonates, acetates or sulfates) may be used.

Of the catalysts of the present invention, those of high bismuth, iron and A component (nickel and/or cobalt) contents are preferred, because they can better reduce sublimation of molybdenum during the oxidation reaction. More specifically, referring to the general formula (1), those complex oxide compositions in which $9 \leq c+d+e$, in particular, $9 \leq c+d+e \leq 20$, are preferred. Hence it is convenient to use, as at least a part of the bismuth-supply source, basic bismuth nitrate, and as the supply sources of iron and A component, compounds containing no or less nitric acid, to render the molar ratio of total nitrate anions to molybdenum not more than 1.8 at the time of preparing the catalyst. Specifically, use of iron hydroxide or the like as the source of iron, and nickel carbonate, nickel acetate, cobalt acetate or the like as the source of A component, is preferred.

The catalysts of the present invention can be prepared by the generally practiced methods for preparing this type of catalysts, from generally used starting materials.

As the starting materials, compounds which produce oxides upon calcination, for example, ammonium salts, nitrates and the like can be used. As the method of preparation, it normally comprises dissolving or dispersing each prescribed amount of staring materials containing the elementary components in an aqueous medium, heating the solution or dispersion under stirring, then evaporating the system to dry solid, drying and grinding the solid and molding the resultant powder into optional form by extrusion molding, making tablets or granulation. In that occasion, inorganic fibers such as glass fiber and various kinds of whiskers, which are generally well known for their effect of improving strength and attrition resistance of catalyst may be added. Also for controlling the catalyst properties with good reproducibility, additives generally known as powder binder such as ammonium nitrate, cellulose, starch, polyvinyl alcohol, stearic acid and the like may be used.

The catalyst of the present invention can be used by itself or may be supported on inert carriers such as alumina, silica-alumina, silicon carbide, titanium dioxide, magnesium oxide, aluminum sponge and the like.

The complex oxide catalysts according to the present invention can be obtained by calcining the molded products or those supported on carriers at 300–600° C. for around 1–10 hours in an air stream.

The complex oxide catalysts of the present invention are favorably used for producing acrolein and acrylic acid by vapor-phase oxidation of propylene; methacrolein and methacrylic acid by vapor-phase oxidation of isobutylene; methacrolein and methacrylic acid by vapor-phase oxidation of t-butanol; and methacrolein and methacrylic acid by vapor-phase oxidation of methyl-t-butyl ether. Needless to say, furthermore, the present invention also covers such an embodiment, taking an example in the vapor-phase oxidation of propylene, of producing mainly acrolein.

Apparatus and operation conditions for practicing the vapor-phase catalytic oxidation reaction of the present invention a subject to no critical limitation. As the reactor, any of generally use&d fixed bed, fluidable bed and mobile bed reactors can be used, and as the reaction conditions those generally used for producing (meth)acrolein and (meth)acrylic acid by vapor-phase catalytic oxidation can be adopted. For example, a gaseous mixture comprising 1–15 vol. % of at least one compound selected from propylene, isobutylene, t-butanol and methyl-t-butyl ether as the starting gas and 1–10 vol. times of the starting gas of molecular oxygen and inert gas which is to serve as a diluent (e.g., nitrogen, carbon dioxide, steam, etc.) is contacted with a catalyst of the present invention at temperatures ranging from 250 to 450° C., under a pressure ranging from 0.1 to 1.0 MPa and at a space velocity ranging from 300 to 5000 $hr^{-1}$ (STP) to carry out the intended reaction.

According to the process of the present invention, acrolein and acrylic acid are produced from propylene; methacrolein and methacrylic acid, from isobutylene; methacrolein and methacrylic acid, from t-butanol; and methacrolein and methacrylic acid, from methyl-t-butyl ether, at high yield.

EFFECT OF THE INVENTION

The catalysts of the present invention can be prepared with good reproducibility, have high activity levels and exhibit high yields. Thus, according to the process of the present invention using the catalysts, (meth)acrolein and (meth)acrylic acid can be produced at high yields with high stability over prolonged period.

EXAMPLES

Hereinafter the present invention is explained more specifically, referring to working Examples, it being understood that the invention is not limited thereto. In the following Examples and Comparative Examples, the conversion, total selectivity and total one-pass yield have the following definitions.

Conversion (mol %)=(mol number of reacted starting compound)/ (mol number of supplied starting compound)×100

Total selectivity (mol %)=(total mol number of formed (meth)acrolein and (meth)acrylic acid)/(mol number of reacted starting compound)×100

Total one-pass yield (mol %)=(total mol number of formed (meth)acrolein and (meth)acrylic acid)/(mol number of supplied starting compound)×100

Example 1

Catalyst Preparation

In 1 liter of ion-exchange water, 550 g of cobalt nitrate, 412 g of nickel nitrate and 286 g of ferric nitrate were dissolved, and 92 g of bismuth nitrate was dissolved in aqueous nitric acid consisting of 50 g of 61 wt. % nitric acid and 200 ml of ion-exchange water. Separately, 1000 g of ammonium paramolybdate and 25 g of ammonium paratungstate were added to 3 liters of heated ion-exchange water, and dissolved under stirring. Into thus formed aqueous solution, the two aqueous solutions which were separately prepared were added dropwise and mixed, and into the mixture then an aqueous solution of 3.8 g of potassium nitrate in 50 ml of ion-exchange water and 141 g of silica sol of 20 wt. % in concentration were added by the order stated. Thereafter 178 g of basic bismuth nitrate (product of Kanto Chemical Co.) was added to the mixture to provide a slurry containing the following elements: Mo, W, Bi, Fe, Co, Ni, K and Si. The molar ratio of the total nitrate anions to the molybdenum [NO$_3$]/[Mo] in this slurry was 1.8.

This slurry was heated under stirring, evaporated to day solid and dried. The resulting solid was pulverized and molded into rings of each 6 mm in outer diameter, 2 mm in inner diameter and 6.6 mm in length, which were calcined at 480° C. for 8 hours in an air stream to provide catalyst (1).

The metal element composition of this catalyst (1) was as follows (in terms of atomic ratio excepting oxygen, as in all of the following Examples):

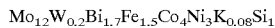

$Mo_{12}W_{0.2}Bi_{1.7}Fe_{1.5}Co_4Ni_3K_{0.08}Si_1$

A stainless steel reactor of 25 mm in diameter was charged with 1500 ml of catalyst (1), and into which a gaseous mixture comprising 7 vol. % of propylene, 14 vol. % of oxygen, 25 vol. % of steam and 54 vol. % of inert gas (nitrogen, etc.) was introduced at a space velocity of 1800 hr$^{-1}$ (STP) and reaction temperature of 310° C. to carry out the oxidation reaction. The result was as shown in Table 1.

Comparative Example 1

Catalyst Preparation

Catalyst (2) was prepared in the same manner as in Example 1, except that no basic bismuth nitrate was added and that the amount of bismuth nitrate was increased to 389 g. [NO$_3$]/[Mo] in this slurry was 2.0.

The metal element composition of this catalyst (2) was same to that of catalyst (1).

Oxidation Reaction

The oxidation reaction of Example 1 was repeated except that catalyst (2) was used in place of catalyst (1). The result was as shown in Table 1.

Comparative Example 2

Catalyst Preparation

Catalyst (3) was prepared in the same manner as in Example 1, except that 137 g of cobalt nitrate and 251 g of cobalt acetate were used as the source of cobalt and 250 g of nickel acetate was used as the source of nickel. The [NO$_3$]/[Mo] ratio in the slurry was 0.8.

The metal element composition of this catalyst was same to that of catalyst (1).

Oxidation Reaction

The oxidation reaction of Example 1 was repeated except that catalyst (3) was used in place of catalyst (1). The result was as shown in Table 1.

Upon comparing Example 1 with Comparative Examples 1 and 2, it is understood that catalyst (1) of the present invention excels over the control catalysts (2) and (3) in catalytic activity and gives high yield.

Example 2

Catalyst Preparation

In 1 liter of ion-exchange water, 137 of cobalt nitrate, 251 g of cobalt acetate, 412 g of nickel nitrate and 286 g of ferric nitrate were dissolved, and 92 g of bismuth nitrate was dissolved in aqueous nitric acid consisting of 50 g of 61 wt. % nitric acid and 200 ml of ion-exchange water. Separately, 1000 g of ammonium paramolybdate and 25 g of ammonium paratungstate were added to 3 liters of ion-exchange water and dissolved under stirring. To the so formed aqueous solution, those separately prepared two aqueous solutions were added dropwise and mixed, and to the mixture an aqueous solution of 3.8 g of potassium nitrate in 50 ml of ion-exchange water and 141 g of silica sol of 20 wt. % in concentration were added by the order stated. Upon further adding 178 g of basic bismuth nitrate (product of Kanto Chemical Co.) to the mixture, a slurry containing the following elements was obtained: Mo, W, Bi, Fe, Co, Ni, K and Si. The [NO$_3$]/[Mo] ratio in the slurry was 1.3.

Using this slurry, catalyst (4) was prepared in the same manner as in Example 1. The metal element composition of this catalyst (4) was as follows:

$Mo_{12}W_{0.2}Bi_{1.7}Fe_{1.5}Co_4Ni_3K_{0.08}Si_1$.

Oxidation Reaction

The oxidation reaction of Example 1 was repeated except that catalyst (4) was used in place of catalyst (1). The result was as shown in Table 1.

Example 3

Catalyst Preparation

In 1 liter of ion-exchange water, 550 g of cobalt nitrate and 286 g of ferric nitrate were dissolved, and thereafter 250 g of nickel acetate was added to the solution. Separately, 389 g of bismuth nitrate was dissolved in aqueous nitric acid consisting of 50 g of 61 wt. % nitric acid and 200 ml of ion-exchange water. Again separately, 1000 g of ammonium paramolybdate and 25 g of ammonium paratungstate were added to 3 liters of heated ion-exchange water and dissolved under stirring. To the resulting aqueous solution, the first two aqueous solutions separately prepared were added dropwise and mixed. To the mixture an aqueous solution of 3.8 g potassium nitrate in 50 ml of ion-exchange water and 141 g of silica sol of 20 wt. % in concentration were added by the order stated, to provide a slurry containing the following elements: Mo, W, Bi, Fe, Co, Ni, K and Si. The [NO$_3$]/[Mo] ratio in this slurry was 1.5.

Using this slurry, catalyst (5) was prepared in the same manner as in Example 1. The metal element composition of this catalyst (5) was as follows:

$$Mo_{12}W_{0.2}Bi_{1.7}Fe_{1.5}Co_4Ni_3K_{0.08}Si_1.$$

Oxidation Reaction

The oxidation Reaction of Example 1 was repeated except that catalyst (5) was used in place of catalyst (1). The result was as shown in Table 1.

TABLE 1

|  | Propylene Conversion % | Acrolein + Acrylic Acid Yield % | Acrolein + Acrylic Acid Selectivity % |
|---|---|---|---|
| Example 1 | 98.5 | 93.7 | 95.1 |
| Comparative Example 1 | 96.2 | 89.6 | 92.3 |
| Comparative Example 2 | 95.3 | 89.5 | 93.9 |
| Example 2 | 98.3 | 93.2 | 94.8 |
| Example 3 | 97.9 | 92.7 | 94.7 |

Example 4

Catalyst Preparation

In 1 liter of ion-exchange water, 893 g of cobalt nitrate, 305 g of ferric nitrate and 10 g of cerium nitrate were dissolved. Separately, 1000 g of ammonium paramolybdate and 64 g of ammonium paratungstate were added to 3 liters of ion-exchange water and dissolved under stirring. To the so formed aqueous solution the other aqueous solution was added dropwise and mixed, and to the mixture an aqueous solution of 55 g of cesium nitrate in 100 ml of ion-exchange water and 273 g of basic bismuth nitrate were added by the order stated, to provide a slurry containing the following elements: Mo, W, Bi, Fe, Co, Ce and Cs. The [NO₃]/[Mo] ratio in the slurry was 1.7.

The same slurry was heated under stirring, evaporated to dry solid and dried. The resulting solid was pulverized and molded into rings of each 6 mm in outer diameter, 2 mm in inner diameter and 6.6 mm in length. The rings were calcined at 500° C. for 8 hours in an air stream to provide catalyst (6) whose metal element composition was as follows:

$$Mo_{12}W_{0.5}Bi_2Fe_{1.6}Co_{6.5}Ce_{0.05}Cs_{0.6}.$$

Oxidation Reaction

A stainless steel reactor of 25 mm in diameter was charged with 1500 ml of catalyst (6), and into said reactor a gaseous mixture composed of 6 vol. % of isobutylene, 14 vol. % of oxygen, 25 vol. % of steam and 55 vol. % of inert gas (nitrogen, etc.) was introduced at a space velocity of 1800 hr⁻¹ (STP) to carry out the oxidation reaction at 340° C. The result was as shown in Table 2.

Comparative Example 3

Catalyst Preparation

The catalyst Preparation of Example 4 was repeated except that 206 g of cobalt nitrate and 418 of cobalt acetate were used as the cobalt source, to provide catalyst (7). The [NO₃]/[Mo] ratio in the slurry was 0.9.

The metal element composition of this catalyst (7) is same to that of catalyst (6).

Oxidation Reaction

The oxidation Reaction in Example 4 was repeated except that catalyst (6) was replaced with catalyst (7). The result was as shown in Table 2.

Comparative Example 4

Catalyst Preparation

Catalyst (8) was prepared in the identical manner with Example 4, except that no basic bismuth nitrate was used and that the amount of bismuth nitrate was increased to 458 g. The [NO₃]/[Mo] ratio in the slurry was 2.1.

The metal element composition of catalyst (8) is same to that of catalyst (6).

Oxidation Reaction

The oxidation Reaction in Example 4 was repeated except that catalyst (8) was used in place of catalyst (6). The result was as shown in Table 2.

Example 5

Catalyst Preparation

In 1 liter of ion-exchange water, 756 g of cobalt nitrate and 381 g of ferric nitrate were dissolved. Separately, 1000 g of ammonium paramolybdate and 64 g of ammonium paratungstate were added to 3 liters of heated ion-exchange water and dissolved under stirring. To the so formed aqueous solution the other aqueous solution was added dropwise, and mixed. To the mixture then an aqueous solution of 55 g of cesium nitrate in 100 ml of ion-exchange water, 273 g of basic bismuth nitrate and 55 g of bismuth oxide were added by the order stated. The [NO₃]/[Mo] ratio in the resulting slurry was 1.6.

Thus obtained slurry was heated under stirring, evaporated to dry solid and dried. The resulting solid was pulverized and molded into rings of 6 mm in outer diameter, 2 mm in inner diameter and 6.6 mm in length, which were calcined at 500° C. for 8 hours in an air stream to provide catalyst (9). The metal element composition of this catalyst (9) was as follows:

$$Mo_{12}W_{0.5}Bi_2Fe_{1.6}Co_{6.5}Ce_{0.05}Cs_{0.6}.$$

Oxidation Reaction

The oxidation Reaction was carried out in the identical manner with that in Example 4, except that catalyst (6) was replaced with catalyst (9). The result was as shown in Table 2.

TABLE 2

|  | Isobutylene Conversion % | Methacrolein + Methacrylic Acid Yield % | Methacrolein + Methacrylic Acid Selectivity % |
|---|---|---|---|
| Example 4 | 98.8 | 87.1 | 88.2 |
| Comparative Example 3 | 96.9 | 84.6 | 87.3 |
| Comparative Example 4 | 95.5 | 83.6 | 87.5 |
| Example 5 | 98.9 | 87.0 | 88.0 |

Example 6

The oxidation Reaction was carried out in the identical manner with that of Example 4, except that t-butanol was used as the starting gas in place of isobutylene. The result was as shown in Table 3.

TABLE 3

|  | t-Butanol Conversion % | Methacrolein + Methacrylic Acid Yield % | Methacrolein + Methacrylic Acid Selectivity % |
|---|---|---|---|
| Example 6 | 100 | 87.2 | 87.2 |

Example 7

The oxidation Reaction was carried out in the identical manner with that in Example 4, except that methyl-t-butyl ether (MTBE) was used as the starting gas in place of isobutylene, and that the space velocity and the reaction temperature were changed to 1200 hr$^{-1}$ (STP) and 350° C., respectively. The result was as shown in Table 4.

TABLE 4

|  | MTBE Conversion % | Methacrolein + Methacrylic Acid Yield % | Methacrolein + Methacrylic Acid Selectivity % |
|---|---|---|---|
| Example 7 | 98.9 | 85.8 | 86.8 |

Example 8

Catalyst Preparation

In 1 liter of ion-exchange water, 756 g of cobalt nitrate and 229 g of ferric nitrate were dissolved, and 137 g of bismuth nitrate was dissolved in aqueous nitric acid composed of 30 g of 61 wt. % nitric acid and 120 ml of ion-exchange water. Separately, 1000 g of ammonium paramolybdate and 63 g of ammonium paratungstate were added to 3 liters of heated ion-exchange water and dissolved under stirring. To thus formed aqueous solution, the first two aqueous solutions separately prepared were added dropwise and mixed, and to the resulting mixture an aqueous solution of 2.4 g of potassium nitrate in 50 ml of ion-exchange water and 191 g of silica sol of 20 wt. % in concentration were added by the order stated. Lastly, 110 g of basic bismuth nitrate (product of Kanto Chemical Co.) was added to the mixture to provide a slurry containing Mo, W, Bi, Fe, Co, K and Si. The [NO$_3$]/[Mo] ratio in this slurry was 1.5.

This slurry was heated under stirring, evaporated to dry solid and dried. The resulting solid was pulverized and molded into cylindrical product of each 6 mm in diameter and 6.6 mm in length, which was calcined at 460° C. for 8 hours in an air stream to provide catalyst (10).

The metal element composition of this catalyst (10) was as follows:

$$Mo_{12}W_{0.2}Bi_{1.4}Fe_{1.2}Co_{5.5}K_{0.05}Si_{1.35}.$$

Oxidation Reaction

The oxidation Reaction as carried out in Example 1 was repeated except that catalyst (10) was used in place of catalyst (1). The result was as shown in Table 5.

When this catalyst (10) (in which c+d+e=8.1) was used in the reaction over many hours, minor reduction in catalytic performance was observed.

Example 9

Catalyst Preparation

Catalyst (11) was prepared in the identical manner with Example 8, except that bismuth nitrate was used in place of basic bismuth nitrate. The [NO$_3$]/[Mo] ratio at the time of the catalyst preparation was 1.6.

Oxidation Reaction

The oxidation Reaction as conducted in Example 1 was repeated except that catalyst (11) was used in place of catalyst (1). The result was as shown in Table 5.

When catalyst (11) was used in the reaction over many hours, minor reduction in catalytic performance was observed similarly to the case of Catalyst (10).

TABLE 5

|  | Propylene Conversion % | Acrolein + Acrylic Acid Yield % | Acrolein + Acrylic Acid Selectivity % |
|---|---|---|---|
| Example 8 | 97.2 | 91.1 | 93.7 |
| Example 9 | 97.1 | 91 | 93.7 |

What is claimed is:

1. A complex oxide catalyst which is expressed by general formula (1):

$$Mo_aW_bBi_cFe_dA_eB_fC_gD_hE_iO_x$$

in which Mo is molybdenum; W is tungsten; Bi is bismuth; Fe is iron; A is at least an element selected from nickel and cobalt; B is at least an element selected from sodium, potassium, rubidium, cesium and thallium; C is at least an element selected from alkaline earth metals; D is at least an element selected from phosphorus, tellurium, antimony, tin, cerium, lead, niobium, manganese, arsenic, boron and zinc; E is at least an element selected from silicon, aluminum, titanium and zirconium; and O is oxygen; a, b, c, d, e, f, g, h, i and x denote the atomic ratios of Mo, W, Bi, Fe, A, B, C, D, E and O, respectively; and where a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$, and x is determined by degree of oxidation of each of the elements, said catalyst being characterized in that it is prepared from an aqueous slurry comprising (i) bismuth nitrate and/or basic bismuth nitrate as bismuth-source compound, (ii) other source compounds for supplying other components than bismuth and (iii) nitric acid, in that the molar ratio of total nitrate anions (NO3) from any of said compounds and nitric acid in said aqueous slurry to molybdenum (Mo) in said aqueous slurry is adjusted to be more than 1 but not more than 1.8.

2. The complex oxide catalyst as defined in claim 1, in which basic bismuth nitrate is used as at least a part of the bismuth-supplying source.

3. The complex oxide catalyst as defined in claim 1 or 2, in which $9 \leq c+d+e \leq 20$.

4. The complex oxide catalyst according to claim 1, wherein, during preparation of said catalyst, it is subjected to calcination at a temperature in the range of from 300 ° C. to less than 600 ° C.

5. The complex oxide catalyst according to claim 1, wherein the molar ratio, nitrate anions (NO$_3$)/molybdenum (Mo), at the time of catalyst preparation, is in the range of from 1.1 to 1.8.

6. A complex oxide catalyst which has the composition represented by the formula $$Mo_{12}W_{0.2}Bi_{1.7}Fe_{1.5}Co_{0.4}Ni_3K_{0.08}Si_1O_x$$

in which Mo is molybdenum; W is tungsten; Bi is bismuth; Fe is iron; A is at least an element selected from nickel and cobalt; B is at least an element selected from sodium, potassium, rubidium, cesium and thallium; C is at least an element selected from alkaline earth metals; D is at least an element selected from phosphorus, tellurium, antimony, tin, cerium, lead, niobium, manganese, arsenic, boron and zinc; E is at least an element selected from silicon, aluminum, titanium and zirconium; and O is oxygen; a, b, c, d, e, f, g, h, i and x denote the atomic ratios of Mo, W, Bi, Fe, A, B, C, D, E and O, respectively; and where a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$, and x is determined by degree of oxidation of each of the elements, said catalyst being characterized in that the molar ratio of total nitrate anions to the molybdenum at the time of the catalyst preparation is adjusted to be more than 1 but not more than 1.8.

7. A complex oxide catalyst which has the composition represented by the formula $$Mo_{12}W_{0.5}Bi_2Fe_{1.6}Co_{6.5}Ce_{0.05}Cs_{0.6}O_x$$

in which Mo is molybdenum; W is tungsten; Bi is bismuth; Fe is iron; A is at least an element selected from nickel and cobalt; B is at least an element selected from sodium, potassium, rubidium, cesium and thallium; C is at least an element selected from alkaline earth metals; D is at least an element selected from phosphorus, tellurium, antimony, tin, cerium, lead, niobium, manganese, arsenic, boron and zinc; E is at least an element selected from silicon, aluminum, titanium and zirconium; and O is oxygen; a, b, c, d, e, f, g, h, i and x denote the atomic ratios of Mo, W, Bi, Fe, A, B, C, D, E and O, respectively; and where a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$, and x is determined by degree of oxidation of each of the elements, said catalyst being characterized in that the molar ratio of total nitrate anions to the molybdenum at the time of the catalyst preparation is adjusted to be more than 1 but not more than 1.8.

8. A complex oxide catalyst which has the composition represented by the formula $$Mo_{12}W_{0.2}Bi_{1.4}Fe_{1.2}Co_{5.5}K_{0.05}Si_{1.35}O_x$$

in which Mo is molybdenum; W is tungsten; Bi is bismuth; Fe is iron; A is at least an element selected from nickel and cobalt; B is at least an element selected from sodium, potassium, rubidium, cesium and thallium; C is at least an element selected from alkaline earth metals; D is at least an element selected from phosphorus, tellurium, antimony, tin, cerium, lead, niobium, manganese, arsenic, boron and zinc; E is at least an element selected from silicon, aluminum, titanium and zirconium; and O is oxygen; a, b, c, d, e, f, g, h, i and x denote the atomic ratios of Mo, W, Bi, Fe, A, B, C, D, E and O, respectively; and where a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$, and x is determined by degree of oxidation of each of the elements, said catalyst being characterized in that the molar ratio of total nitrate anions to the molybdenum at the time of the catalyst preparation is adjusted to be more than 1 but not more than 1.8.

9. A multimetal catalyst oxide useful for catalyzing the vapor phase oxidation of propylene, isobutylene, t-butanol, t-butanol, and/or methyl-t-butyl ether to produce (meth) acrolein or (meth)acrylic acid, said catalyst having a composition expressed by the following general formula (1):

$$Mo_aW_bBi_cFe_dA_eB_fC_gD_hE_iO_x \qquad (1)$$

wherein Mo represents molybdenum; W, represents tungsten, Bi represents bismuth, A represents at least one of nickel and cobalt, C represents at least one of alkaline earth metal, D represents at least one of phosphorus, tellurium, antimony, tin, cerium, lead, niobium, manganese, arsenic, boron and zinc, E represents at least one of silicon, aluminum, titanium, and zirconium; and O represents oxygen; a, b, c, d, e, f, g, h, i, and x denote the atomic ratios of Mo, W, Bi, Fe, A, B, C, D, E, and O, respectively; and when a is 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$ and $0 \leq i \leq 30$, and x is a numerical value determined by degree of oxidation of each of the elements; said catalyst being characterized in that it is prepared from an aqueous slurry comprising (i) bismuth nitrate and/or basic bismuth nitrate as bismuth-source compound, (ii) other source compounds for supplying other components than bismuth and (iii) nitric acid, in that the molar ratio of total nitrate anions ($NO_3$) from any of said compounds and nitric acid in said aqueous slurry to molybdenum (Mo) in said aqueous slurry is adjusted to be more than 1 but not more than 1.8.

* * * * *